United States Patent
Ande et al.

(10) Patent No.: US 9,781,909 B2
(45) Date of Patent: Oct. 10, 2017

(54) MITO-OB: A TRANSGENIC MOUSE MODEL FOR OBESITY

(71) Applicant: University of Manitoba, Winnipeg (CA)

(72) Inventors: Sudharsana R. Ande, Winnipeg (CA); Suresh Mishra, Winnipeg (CA)

(73) Assignee: University of Manitoba, Winnipeg, Manitoba (CA)

( * ) Notice: Subject to any disclaimer, the term of this patent is extended or adjusted under 35 U.S.C. 154(b) by 0 days.

(21) Appl. No.: 14/328,888

(22) Filed: Jul. 11, 2014

(65) Prior Publication Data

US 2015/0026833 A1    Jan. 22, 2015

Related U.S. Application Data

(60) Provisional application No. 61/847,160, filed on Jul. 17, 2013.

(51) Int. Cl.
*A01K 67/027* (2006.01)
*C07K 14/47* (2006.01)

(52) U.S. Cl.
CPC ...... *A01K 67/0276* (2013.01); *A01K 67/0275* (2013.01); *C07K 14/4703* (2013.01); *A01K 2227/105* (2013.01); *A01K 2267/0362* (2013.01); *C12N 2830/008* (2013.01)

(58) Field of Classification Search
USPC .......................................................... 800/18
See application file for complete search history.

(56) References Cited

U.S. PATENT DOCUMENTS

| | | | | |
|---|---|---|---|---|
| 5,658,792 A | * | 8/1997 | Nuell ................. | C07K 14/4703 435/252.3 |
| 2004/0216176 A1 | * | 10/2004 | MacDougald ..... | A01K 67/0275 800/14 |
| 2005/0032761 A1 | * | 2/2005 | Morton ................. | A61K 31/00 514/177 |
| 2006/0179501 A1 | * | 8/2006 | Chan ................. | A01K 67/0275 800/18 |

OTHER PUBLICATIONS

Masuzaki (Sci 2001, vol. 294, p. 2166-2170).*
Mishra (J Cell. Mol. Med. 2006, vol. 10, No. 2, p. 353-363).*
Cowan (Xenotransplantation, 2003, vol. 10, p. 223-231).*
Ageta-Ishahara (Molecular Brain, 2013, 6:35, p. 1-14).*
Sato (Cancer Res., 1992, vol. 52, p. 1643-1646).*
Theiss (Biochim Biophys Acta Jun. 2011, vol. 1813, No. 6, p. 1137-1143).*
Thuaud (Chem. & Biol. Rev., 2013, vol. 20, p. 316).*

* cited by examiner

*Primary Examiner* — Michael Wilson
(74) *Attorney, Agent, or Firm* — Michael R. Williams; Ade & Company Inc.

(57) ABSTRACT

An obese mouse model was developed by overexpressing the mitochondrial protein prohibitin (PHB) in white adipose tissue (WAT) specific manner driven by adipocyte protein 2 (aP2) promoter. These mice begin to develop obesity as a result of mitochondrial remodeling (upregulation of mitochondrial biogenesis and function) in WAT.

12 Claims, 4 Drawing Sheets

SEQUENCE LISTING

```
<160> NUMBER OF SEQ ID NOS: 4

<210> SEQ ID NO 1
<211> LENGTH: 826
<212> TYPE: DNA
<213> ORGANISM: mouse

<400> SEQUENCE: 1
aaagggaaca aaagctggag ctccaccgcg gtggagctcg agtcagtgag cgaggaagcg      60
gaagagtcta gagtcgacca gacatgataa gatacattga tgagtttgga caaaccacaa     120
ctagaatgca gtgaaaaaaa tgctttattt gtgaaatttg tgatgctatt gctttatttg     180
taaccattat aagctgcaat aaacaagttc tgctttaata agatctgatt cgaattccaa     240
gcttggatcc gaattcgccc tatagtgagt cgtattacgc ggccgctcta gaactagtgg     300
atcccccggg ctgcagcaca ggagggtgct atgagcctct gaagtccaga tagctcactt     360
ttaaagatgc cctgaccatg tgactgtagg agtgaccaat gggggccaga tcatttcctt     420
catgaccaga ccctgtatgt tttcctctga gtcatgtttt taatagaaat ttctcaactt     480
tggttctccc tggcaatgat cactggactt agagtacaaa ttattttaa ccatgaacag      540 agtattttaa aggttcctgt tttgactgtc aaaagctaat gcattgaact tccccccatt     600
attccttatg gatttgcctc attgtggagg agacaattat cttggacaca tttgaccttc     660
ttatcttgag tttttatttt attaatactg caataatgtg tttagttctt ctgaatttga     720
```

```
gaacataaaa actatcttag agattcttag tcttaatggc tcttttgtta gaatagtgtt    780
tatctcacga atttaacaa ataaataat gacatttaa agtagc                      826

<210> SEQ ID NO 2
<211> LENGTH: 992
<212> TYPE: DNA
<213> ORGANISM: mouse

<400> SEQUENCE: 2
gaattcggca cgaggggaat tcatgtggag gtcagagtgg aagcaggtgt gagagggtcc     60
agcagaagga aacatggctg ccaaagtgtt tgagtccatt ggcaagtttg gcctggcctt    120
agctgttgca ggaggcgtgg tgaactctgc cttatataat gtggatgctg ggcacagagc    180
tgtcatcttt gaccgattcc gtggagtgca ggacattgtg gtaggggaag ggactcattt    240
tctcatcccg tgggtacaga aaccaattat ctttgactgc cgttctcgac cacgtaatgt    300
gccagtcatc actggtagca aagatttaca gaatgtcaac atcacactgc gcatcctctt    360
ccggcctgtc gccagccagc ttcctcgcat cttcaccagc atcggagagg actatgatga    420
gcgtgtgctg ccgtccatca caactgagat cctcaagtca gtggtggctc gctttgatgc    480
tggagaacta atcacccaga gagagctggt ctccaggcag gtgagcgacg accttacaga    540
gcgagccgcc acctttgggc tcatcctgga tgacgtgtcc ttgacacatc tgaccttcgg    600
gaaggagttc acagaagcgg tggaagccaa acaggtggct cagcaggaag cagagagggc    660
cagatttgtg gtggaaaagg ctgagcaaca gaaaaaggcg gccatcatct ctgctgaggg    720
cgactccaag gcagctgagc tgattgccaa ctcactggcc actgcagggg atggcctgat    780
cgagctgcgc aagctggaag ctgcagagga catcgcgtac cagctctcac gctctcggaa    840
catcacctac ctgccagcgg ggcagtccgt gctcctccag ctgccccagt gagggcccac    900
cctgcctgca cctccgcggg ctgactgggc cacagccccg atgattctta acacagcctt    960
ccttctgctc ccaccccaga aatcactgtg aa                                  992

<210> SEQ ID NO 3
<211> LENGTH: 20
<212> TYPE: DNA
<213> ORGANISM: artificial
<220> FEATURE:
<223> OTHER INFORMATION: Primer for identification of transgene
      positives

<400> SEQUENCE: 3
gcagcccggg ggatccacta                                                 20

<210> SEQ ID NO 4
<211> LENGTH: 32
<212> TYPE: DNA
<213> ORGANISM: artificial
<220> FEATURE:
<223> OTHER INFORMATION: primer for identification of transgene
      positives

<400> SEQUENCE: 4
gcacacgctc atcaaagtcc tctccgatgc tg                                   32
```

MITO-OB: A TRANSGENIC MOUSE MODEL FOR OBESITY

PRIOR APPLICATION INFORMATION

The instant application claims the benefit of U.S. Provisional Patent Application 61/847,160, filed Jul. 17, 2013.

BACKGROUND OF THE INVENTION

Obesity is a significant health problem. Obesity has reached epidemic proportions globally, and the World Health Organization estimates that there are more than 1 billion overweight adults (BMI of 25.0-29.9), of which at least 300 million are obese (BMI of 30 or above) (Kanavos et al. 2012; WHO). Obesity is associated with premature death through increasing the risk of many chronic diseases, including type 2 diabetes, cardiovascular disease, and certain cancers (Kopelman 2007; Guh et al. 2009). In addition, obesity is associated with respiratory difficulties, chronic musculoskeletal problems, lumbago, skin problems, and infertility (Brown et al. 2009). Most of the evidence proposing obesity-associated health problems has been obtained from epidemiological analyses of human subjects; the precise molecular mechanisms of obesity-associated health problems have not yet been determined (Kanasaki and Koya 2010). To better understand the underlying mechanisms of human disease, good animal models are essential. In addition, as the prevalence of obesity is rising with its socioeconomic consequences, the quest to find new treatments or a cure is also increasing. Pharmaceutical treatment is one avenue that has been pursued, but currently there are only a limited number of compounds on the market because many have failed or been withdrawn because of side effects (Nilsson et al. 2011). Given that the developmental process from initial idea to marketed product typically requires more than 10 years and the attrition rate is notably high, it is important that animal models used are good surrogates for human obesity. A number of obese rodent models (e.g. ob/ob, NZO, ZDF and diet-induced obesity (DIO)) are currently used for the discovery and preclinical testing of anti-obesity and anti-diabetic drugs (Kanasaki and Koya 2010). These obese rodent models have some similarities as well as some differences with obesity in humans. For example, most obese humans do not have leptin deficiency; instead, they have hyperleptinemia and leptin resistance and thus generally do not respond with weight loss during recombinant leptin treatment. This finding underlines the fact that although the ob/ob mouse is indeed a valuable and useful animal model of obesity, it does not reflect the complete background of obesity in humans and will therefore not always be predictive of the effect of pharmacological treatments in humans. Similarly, one of the drawbacks of the DIO rodent models is highly variable phenotype due to genetic background of the rodent species used. In addition, DIO models develop hyperinsulinemia but not always hyperglycemia, thereby making them good models for obesity but not necessarily for type 2 diabetes. Likewise, there are some advantages and disadvantages in other rodent models currently used in pre-clinical testing such as db/db mice, Zucker rats and NZO mice models.

Most of obese animal models currently used have been either selected through inbreeding or characterized following spontaneously arising mutations and are often associated with increased food intake (Shafrir and Ziv, 2009). Irrespective of the origin, obesity is characterized by increase in adipose tissue mass and involves corresponding changes in adipose tissue to synthesize and store excess fat. However, obese animal model based on primary alterations in adipose tissue independent of increase food intake or other defects is not available.

Thus, there is a tremendous need for obese animal models for preclinical testing that better mimic the development of obesity and type 2 diabetes in humans in order to better understand the molecular mechanisms of obesity and obesity-associated health problems.

WAT Mitochondria in Whole Body Energy Homeostasis:

A major role has been established for white adipose tissue (WAT) in regulating energy intake, energy expenditure, and insulin sensitivity (Guilherme et al. 2008; Kusminski and Scherer 2012). In addition, recent studies have highlighted the potential relevance of WAT mitochondria in the cellular physiology of the adipocyte and its impact on systemic metabolic regulation (Kusminski and Scherer 2012; De Pauw et al 2009). The adipocyte interprets nutritional and hormonal cues in its microenvironment, and then coordinates its mitochondrial response either to oxidize incoming fatty acid and carbohydrate fuels through the tricarboxylic acid cycle and the respiratory chain, or to store these fuels safely in the form of triglycerides until whole-body energy requirements signal for their release (Sun et al. 2011). Through their ability to influence key biochemical processes central to the adipocyte, such as fatty acid esterification and lipogenesis, as well as their impact upon the production and release of key adipokines, mitochondria play a crucial role in adipose tissue homeostasis and determining systemic insulin sensitivity (Kusminski and Scherer 2012; Rong et al. 2007; Wilson-Fritch et al. 2004). The synchronized initiation of adipogenesis and mitochondrial biogenesis indicates that mitochondria play a pertinent role in the differentiation and maturation of adipocytes (De Pauw et al 2009; Lu et al. 2010).

PHB in Mitochondrial Biology and Adipogenesis:

Prohibitin (PHB, also known as PHB1) is an evolutionarily conserved protein that functions as a mitochondrial chaperone and has a role in mitochondrial biogenesis (Merkwirth and Langer 2009). The PHB gene has been mapped to the chromosome17q12-q21 locus in humans (Sato et al. 1992). The locus 17q21 has been identified among chromosomal regions harboring genes influencing the propensity to store fat in the abdominal area in a genome-wide scan (Perusse et al. 2001). The siRNA-mediated knockdown of PHB in *Caenorhabditis elegans* results in significant reduction in intestinal fat content (Artal-Sanz and Tavernarakis 2009). In addition, using 3T3-L1 preadipocytes we have recently shown that PHB is an important target gene during adipogenesis (Ande et al. 2012). Overexpression of PHB in preadipocyte facilitates adipogenesis whereas silencing PHB has inhibitory effect on mitochondrial biogenesis and adipogenesis (Ande et al. 2012; Liu et al. 2012). In addition, we have shown that PHB inhibits insulin-stimulated fatty acid and glucose oxidation in adipose tissue, which is mediated through pyruvate carboxylase (Vessal et al. 2006), an important enzyme in de novo fatty acid synthesis and glyceroneogenesis (Jitrapakdee et al. 2006). Collectively, these evidences point towards a critical role of PHB in adipose tissue homeostasis.

SUMMARY OF THE INVENTION

According to a first aspect of the invention, there is provided a transgenic mouse comprising increased adipose tissue mass as compared to a wild-type mouse of the same strain and an exogenous nucleic acid construct that comprises a promoter operably linked to a gene encoding prohibitin.

According to a further aspect of the invention, there is provided a transgenic mouse, comprising a transgene, said transgene comprising a polynucleotide encoding a mouse prohibitin protein operably linked to at least a portion of a regulatory region of a mouse aP2 promoter, wherein said transgenic mouse develops obesity compared to a wild type mouse of the same strain.

According to another aspect of the invention, there is provided a transgenic mouse whose genome comprises: a DNA transgene encoding prohibitin.

According to yet another aspect of the invention, there is provided a mouse transgenic fertilized egg comprising an expression construct comprising (a) a nucleotide sequence encoding prohibitin and (b) a transcription-regulating sequence operatively linked to the nucleotide sequence.

According to another aspect of the invention, there is provided an isolated totipotent mouse cell comprising an exogenous nucleic acid construct that comprises prohibitin operably linked to a suitable promoter.

DESCRIPTION OF THE PREFERRED EMBODIMENTS

Figure 1:
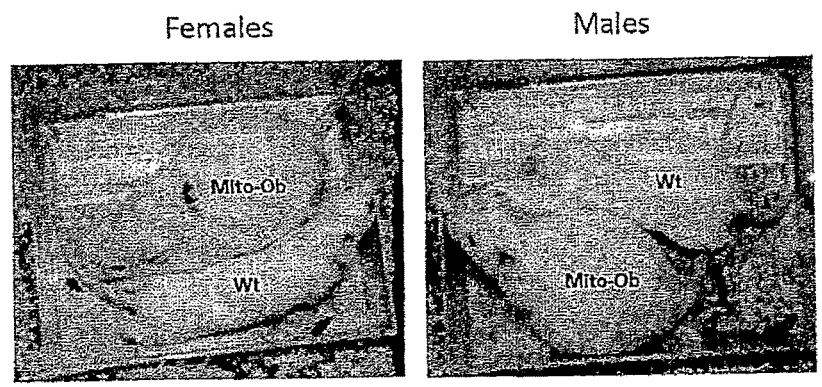
FIG. 1. Photographs showing six months old Mito-Ob female and male mice with their Wild-type (Wt) littermates.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As discussed above, most of obese animal models currently used have been either selected through inbreeding or characterized following spontaneously arising mutations and are often associated with increased food intake and reduced energy expenditure (Shafrir and Ziv, 2009). Irrespective of the origin, obesity is characterized by increase in adipose tissue mass and involves corresponding changes in adipose tissue to synthesize and store excess fat. However, an obese animal model based on primary changes in adipose tissue or other defects is not available.

As discussed herein, the inventors have developed an obese mouse model by overexpressing the mitochondrial protein prohibitin (PHB) in white adipose tissue (WAT) specific manner driven by adipocyte protein 2 (aP2) promoter. The inventors have named these mice "Mito-Ob" because they begin to develop obesity as a result of mitochondrial remodeling (upregulation of mitochondrial biogenesis and function) in WAT, thus are comparable to polygenic obese rodent models.

According to an aspect of the invention, there is provided a transgenic mouse comprising increased adipose tissue mass as compared to a wild-type mouse of the same strain and an exogenous nucleic acid construct that comprises a promoter operably linked to a gene encoding prohibitin.

As discussed below, preferably the prohibitin gene comprises the nucleotide sequence as set forth in SEQ ID No:2.

The promoter may be adipocyte protein 2 (aP2) promoter and the aP2 promoter may comprise the nucleotide sequence as set forth in SEQ ID No:1.

The exogenous nucleic acid construct may be integrated into the mouse genome.

According to another aspect of the invention, there is provided a transgenic mouse, comprising a transgene, said transgene comprising a polynucleotide encoding a mouse prohibitin protein operably linked to at least a portion of a regulatory region of a mouse aP2 promoter, wherein said transgenic mouse develops obesity compared to a wild type mouse of the same strain. As will be appreciated by one of skill in the art, obesity in this context refers to at least an increase in adipose tissue. As discussed herein, the male transgenic mice described are also insulin resistant.

Preferably, the prohibitin protein comprises an amino acid sequence deduced from the nucleotide sequence as set forth in SEQ ID No:2.

Preferably, the aP2 promoter comprises the nucleotide sequence as set forth in SEQ ID No:1.

The transgene may be integrated into the mouse genome.

According to another aspect of the invention, there is provided a transgenic mouse whose genome comprises: a DNA transgene encoding prohibitin.

The prohibitin may be encoded by the nucleotide sequence as set forth in SEQ ID No:2.

The transgene may be operably linked to aP2 promoter and the aP2 promoter may have the nucleotide sequence as set forth in SEQ ID No:1.

According to another aspect of the invention, there is provided a mouse transgenic fertilized egg comprising an expression construct comprising (a) a nucleotide sequence encoding prohibitin and (b) a transcription-regulating sequence operatively linked to the nucleotide sequence.

As will be appreciated by one of skill in the art, such a fertilized egg comprising the expression construct may be generated using a variety of means known in the art. The fertilized egg may then be implanted into a suitable host for generation of a transgenic mouse as described above.

Preferably, the nucleotide sequence encoding prohibitin comprises the nucleotide sequence as set forth in SEQ ID No:2.

The transcription-regulating sequence may be aP2 promoter.

Preferably, the aP2 promoter comprises the nucleotide sequence as set forth in SEQ ID No:1.

Preferably, the expression construct is integrated into the genome of the mouse transgenic fertilized egg.

According to another aspect of the invention, there is provided an isolated totipotent mouse cell comprising an exogenous nucleic acid construct that comprises prohibitin operably linked to a suitable promoter.

Preferably, the exogenous nucleic acid construct encoding prohibitin comprises the nucleotide sequence as set forth in SEQ ID No:2.

Preferably, the suitable promoter comprises aP2 promoter.

Preferably, the aP2 promoter comprises the nucleotide sequence as set forth in SEQ ID No:1.

Preferably, the exogenous nucleic acid construct is integrated into the genome of the mouse cell.

As discussed herein, Mito-Ob male mice develop insulin resistance in addition to obesity and they do not develop overt diabetes. In this aspect, the Mito-Ob mice share similarities with a large portion of human obese population, the group who are both obese and insulin resistance but are not diabetic, as discussed below. The Mito-Ob mice therefore are a valuable animal model for obesity and metabolic syndrome. Further, as discussed herein, Mito-Ob male mice frequently show hyperglycemia thus in this aspect are similar to ZDF, UCD-T2DM rats and NZO mice, which are widely used for studies of anti-obesity and anti-diabetic drugs (Nilsson et al 2011). Thus, Mito-Ob mice are unique in their initiation of obesity that shares features of both polygenic DIO models and a number of monogenic obese rodent models.

Consequently, the Mito-Ob mice are very useful not only in the discovery and development of anti-obesity drugs but also in revealing the role of WAT mitochondria in systemic energy homeostasis and in the identification of novel target genes for the treatment of obesity.

During the last three decades, the prevalence of obesity has grown rapidly including children and youth (Pulgaron 2013). Although factors that led to such a rapid increase in obesity are not understood, transgenerational inherited factors appear to play an important role. For example, epidemiological and animal studies suggest that pre- or peri-conceptional obesity of the mother or environmental exposures early in life may affect metabolic programming in the offspring (Tanumihardjo et al. 2007; Levin 2006; Boer-schmann et al 2010). In addition, new evidence suggests that paternal metabolic state may have similar influence in offspring. Irrespective of its origin from maternal or paternal health status, these transgenerational effects are now being explained by disruptions at the level of epigenetic machinery (Soubry et al. 2013). The Mito-Ob mice provide an opportunity to determine the effect of parental obesity, alone or combined together, with and without insulin resistance on the development of obesity in adult offspring in both F1 and F2 generations.

For example, Mito-Ob male mice may be crossed with wild-type female mice of similar genetic background or vice versa. In this way the offspring will be exposed to either paternal or maternal obese environment; making it possible to then observe and compare health problems in Mito-Ob and non-Mito-Ob adult offspring. Another scenario would be to cross heterozygous Mito-Ob male and female mice and then observe health problems in adult offspring as a consequence of exposure to the obese environment of both parents. It is of note that suitable partners for mating will be readily apparent to one of skill in the art and/or may be readily determined, depending of course on the specific environment desired.

The novel Mito-Ob mouse models provide unique opportunities for the discovery and testing new drugs and identification of novel targets for the treatment of obesity and potentially type 2 diabetes.

As described herein, the Mito-Ob male mice develop obesity, insulin resistance and hyperglycemia in a progressive manner thus provide a larger and distinct windows for the discovery and testing of anti-obesity and anti-diabetic drugs.

As will be readily apparent to one of skill in the art, a wide variety of specific, well-defined diets for animal research are available commercially. For example, high fat, high protein or high carbohydrate diets may be used. Consequently, as discussed herein, improved new models of progressive development of obesity and type 2 diabetes can be developed by manipulating diet or by crossing Mito-Ob mice with other mice models of obesity and type 2 diabetes.

In addition, the Mito-Ob mice are useful to define if the impact is mediated through epigenetic machinery (beyond F2 generations) or simply a manifestation of exposures to parental obesity during pre-conceptional and prenatal life.

For example, transgenerational obesity may be mediated through an epigenetic mechanism or simply by toxic effects of environmental exposures including the obese environment of the parents. To distinguish the precise mechanism involved and to confirm the involvement of epigenetics, it is important to study the effect in offspring beyond second (F2) generation. For example, the germ cells develop during fetal life. So an obese pregnant mother can potentially affect/expose not only her baby (F1 generation) but also the germ cells of the baby that are going to produce the second generation (F2).

Furthermore, the transgenic mice can also be used to determine whether therapeutic intervention in obese parents during or before pregnancy would reduce obesity development in adult offspring.

The transgenic mice can also be used to investigate how the offspring born to obese parents would respond to postnatal environmental determinants (e.g. diet) on the development of obesity and type 2 diabetes.

The transgenic mice can be used to study the underlying mechanisms involved in these processes and in the identification of obesity biomarkers with special emphasis on WAT mitochondria.

The transgenic mice can be used to investigate the underlying mechanisms involved in the crosstalk between the nucleus and mitochondria that is critical for mitochondrial biogenesis.

On the basis of observed phenotype of Mito-Ob mice, it is anticipated that these mice will also develop obesity and type 2 diabetes associated health complications thus provide additional use of this novel mouse model.

In general, excess calorie intake along with reduced energy expenditure has been considered as the cause of obesity and this is supported by a number of rodent obese models (Chua et al. 2007; Hummel et al. 1966; Trayhurn et al. 1982). However, the initiation of obesity development independent of excess calorie intake has not been well explored. For example, changes in the structural and functional components of WAT mitochondria, which have been suggested to have a role in the cellular homeostasis of the adipose tissue and whole body energy homeostasis, may create such a condition. However, there remain critical gaps in our understanding of the relevance of WAT mitochondria in adipose tissue energy homeostasis and their impact upon systemic energy homeostasis. This gap in knowledge may be attributed in part to the lack of obese animal model based on mitochondria remodeling in WAT specific manner, because the majority of the obese animal models used for research studies develop obesity as a result of excess calorie intake. To reduce this critical gap in our knowledge and to explore the possibility of the initiation of obesity independent of high calorie intake, we developed "Mito-Ob" mouse models by overexpressing the mitochondrial protein PHB in WAT specific manner. PHB is an important protein in mitochondrial biogenesis and function and the consequences of its expression in adipocytes are hitherto unknown. Our preliminary observations suggest that the Mito-Ob mice begin to develop obesity as a result of mitochondrial remodeling that is independent of increased food intake. Thus, our novel obese mouse models provide a unique opportunity to study the development of obesity from WAT perspective especially WAT mitochondria.

The inventors hypothesized that upregulation of mitochondrial biogenesis and function in WAT specific manner will lead to increased adipose tissue mass. The obese phenotype of Mito-Ob mice overexpressing mitochondrial protein prohibitin (PHB), known to be involved in mitochondrial biogenesis and function, in WAT specific manner confirms this hypothesis (FIG. 1). This would suggest that an upregulation of mitochondrial biogenesis and function in WAT as a result of environmental exposures might in part underlie obesity development in humans that is currently unexplored.

It is of note that obese rodent modes based on primary changes in white adipose tissue were not previously available. Furthermore, it was not previously possible to investigate the role of WAT mitochondria in adipose tissue and systemic metabolic regulation. However, this model opens the possibility of initiation of obesity development due to primary changes in adipose tissue including adipose tissue mitochondria. Increased food intake may be a manifestation of such changes in the body.

Figure 3:
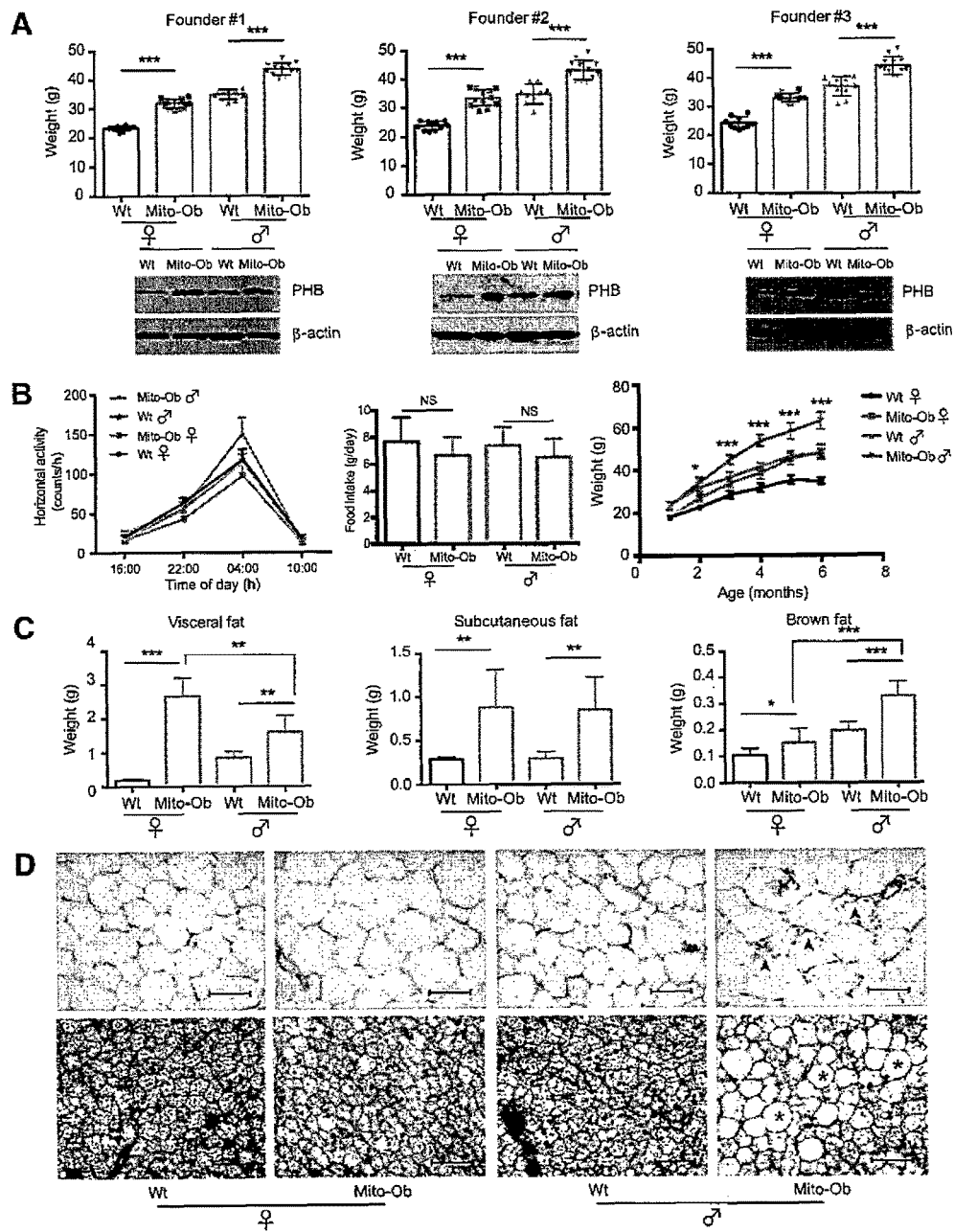
FIG. 3. Growth curve and adipose tissue weight in the Mito-Ob mice. (A) Upper panel: Histograms showing body weight of the Mito-Ob mice and their wild-type (Wt) littermates from three different transgenic lines at three months of age (n=8 to 10 mice in each group). Lower panel: Representative immunoblots showing prohibitin expression levels in the WAT from three different Mito-Ob lines as shown above (n=3). (B) Left panel: Line graphs showing horizontal activity levels in Mito-Ob mice and their Wt littermates. Middle panel: Histograms showing food intake in Mito-Ob mice during 3 to 6 months of age (n=8 to 12 mice in each group). Right panel: Line graph showing growth curve of the Mito-Ob mice and their Wt littermates (n=10 to 12 mice in each group). Asterisk signs applicable to both sexes in comparison with respective wild-type mice. (C) Histograms showing adipose tissue weight of 6 months old mice. (n=8 mice in each group). (D) Upper panel: Representative photomicrographs showing hematoxylin-eosin stained white adipose tissue (WAT) from 6 months old mice (n=6 mice in each group). A crown like structure, a sign of macrophage infiltration, is indicated with black arrowhead (➤). Scale bars, 20 µm. Lower panel: Representative photomicrographs showing hematoxylin-eosin staining of brown adipose tissue (BAT) from 6 months old mice (n=6 mice in each group). Large unilocular lipid droplets are shown with asterisk (*). Scale bars, 20 µm. Data are presented as mean±SEM. Asterisks indicate comparison between sex matched Mito-Ob vs Wt. * P<0.05,  P<0.01, * P<0.001 by Student's t test. NS, not significant.

To further establish the role of PHB in adipose tissue homeostasis at the systems level and the role of WAT mitochondria in whole body metabolism, we developed Mito-Ob mouse models by overexpressing PHB in WAT specific manner. As expected, both male and female transgenic mice start to gain weight from 3-4 weeks onward, become obese by 3-4 months, however only male transgenic mice become insulin resistant between 6-9 months of age in comparison to wild-type (Wt) control littermates (FIG. 3B).

As discussed herein, the obese phenotype of Mito-Ob mice affirms the emerging notion that prohibitin and adipocyte mitochondria have a role in the regulation of adipose tissue homeostasis and metabolic regulation (Wilson-Fritch et al., 2004; Lu et al., 2010; De pauw et al., 2009; Ande et al., 2012; Artal-Sanz et al., 2009; Liu et al., 2012; Kang et al., 2013). However, the metabolic consequences of obesity in the Mito-Ob mice are sex specific. This would suggest that intrinsic differences exist in the way adipose tissues are regulated and/or respond to obesity development in male and female mice despite similar underlying cause. The aP2 promoter used in this study is primarily expressed in adipocytes and it has been used recently in a similar work (Kusminski et al., 2012). In addition, it is expressed in immune cells such as macrophages (Fu et al., 2006). However, a similar effect of PHB manipulation in adipocytes in vitro and in vivo (Ande et al., 2012; Artal-Sanz et al., 2009; Liu et al., 2012; Kang et al., 2013) would suggest that the phenotype observed is most likely due to the role of PHB in adipocytes.

PHB translocates between mitochondria to the nucleus in response to estrogen (Dong et al, 2013). In addition, PHB has been associated with the function of mitochondrial transcription factor A (Tfam) and nuclear factor-like 2 (Nrf-2) (Kasashima et al., 2008; Theiss et al., 2009). Tfam has important roles in mitochondrial biology and Nrf-2 regulates transcription of nuclear-encoded mitochondrial proteins (Kasashima et al., 2008; Athale et al., 2012). These evidences along with the finding of upregulation of mitochondrial biogenesis in the WAT of the Mito-Ob mice would suggest a potential role of PHB in mito-nuclear crosstalk that is required for mitochondrial biogenesis. Furthermore, the upregulation mitochondrial biogenesis markers in the WAT of Mito-Ob mice suggest that PHB indeed has a role in this process. An enhanced mito-nuclear crosstalk may be the underlying mechanism behind increased mitochondrial biogenesis in the WAT of Mito-Ob mice.

Men and women have distinct distributions of their body fat, where subcutaneous fat tends to be predominant in females, whereas visceral fat is predominant in males (Bjorntorp, 1996). It is the visceral fat that is related to obesity and its complications (Bjorntorp, 1996). However, the paradox of normal insulin sensitivity along with increased visceral obesity in the Mito-Ob female mice would suggest that it is not the visceral obesity per se, but rather the functional status of the adipose tissue such as the dynamics of lipid handling and adipokines secretion that leads to obesity associated disorders. For example, a differential regulation of adiponectin in Mito-Ob male and female mice could be related to their different metabolic status, as adiponectin promotes adipocyte differentiation, insulin sensitivity, and lipid accumulation (Fu et al., 2005); and adiponectin secretion has been reported to correlate with mitochondrial function (Wang et al., 2013). In this context it should be noted that estrogens, which have protective effects against obesity also have a role in mitochondrial biogenesis (Bjorntorp, 1996; Chen et al., 2009; Yao et al., 2013). However, it is not known whether the role of estrogen in mitochondrial biology is linked to its protective effect against obesity. The Mito-Ob female mice provide a unique opportunity to dissect the relationship between estrogen, prohibitin, and mitochondria in adipose tissue biology and in metabolic regulation.

In summary, the obese phenotype and sex specific metabolic dysregulation in Mito-Ob mice established for the first time an important role of PHB in adipose tissue biology in mammals. Mito-Ob mice provide a valuable tool for obesity research. Mito-Ob mice can be used to better define the sex differences in obesity and associated health problems, and the potential role of adipose tissue mitochondria.

The invention will now be further described by way of examples. However, the invention is not necessary limited to or by the examples.

Cloning of PHB in aP2 Promoter Containing Vector:

The aP2 promoter-containing vector (pBS-aP2 promoter (5.4 kb) polyA) was obtained from Addgene (Cambridge, Mass.). Full length PHB clone was obtained from Origene, USA (Cat # SC110973). This clone was digested with Not1 to release the full-length cDNA of PHB. Subsequently PHB cDNA was sub-cloned into the Not1 site of pBS-aP2 promoter vector. The authenticity of the construct was confirmed by DNA sequencing at the Cancer Care Manitoba, Canada.

```
pBS-aP2 promoter
                                           (SEQ ID NO: 1)
AAAGGGAACA AAAGCTGGAG CTCCACCGCG GTGGAGCTCG

AGTCAGTGAG CGAGGAAGCG GAAGAGTCTA GAGTCGACCA

GACATGATAA GATACATTGA TGAGTTTGGA CAAACCACAA

CTAGAATGCA GTGAAAAAAA TGCTTTATTT GTGAAATTTG

TGATGCTATT GCTTTATTTG TAACCATTAT AAGCTGCAAT

AAACAAGTTC TGCTTTAATA AGATCTGATT CGAATTCCAA

GCTTGGATCC GAATTCGCCC TATAGTGAGT CGTATTACGC

GGCCGCTCTA GAACTAGTGG ATCCCCCGGG CTGCAGCACA

GGAGGGTGCT ATGAGCCTCT GAAGTCCAGA TAGCTCACTT
```

```
-continued
TTAAAGATGC CCTGACCATG TGACTGTAGG AGTGACCAAT

GGGGGCCAGA TCATTTCCTT CATGACCAGA CCCTGTATGT

TTTCCTCTGA GTCATGTTTT TAATAGAAAT TTCTCAACTT

TGGTTCTCCC TGGCAATGAT CACTGGACTT AGAGTACAAA

TTATTTTTAA CCATGAACAG AGTATTTTAA AGGTTCCTGT

TTTGACTGTC AAAAGCTAAT GCATTGAACT TCCCCCCATT

ATTCCTTATG GATTTGCCTC ATTGTGGAGG AGACAATTAT

CTTGGACACA TTTGACCTTC TTATCTTGAG TTTTTATTTT

ATTAATACTG CAATAATGTG TTTAGTTCTT CTGAATTTGA

GAACATAAAA ACTATCTTAG AGATTCTTAG TCTTAATGGC

TCTTTTGTTA GAATAGTGTT TATCTCACGA ATTTTAACAA

AATAAATAAT GACATTTTAA AGTAGC               826
```

>OriGene sequence for PHB (NM_002634) (SEQ ID NO:2)

PHB sequence begins here at "G" (shown with arrow); translation initiation site (ATG) shown below in "underline"

```
               ↓
GAATTCGGCA CGAGGGGAAT TCATGTGGAG GTCAGAGTGG

AAGCAGGTGT GAGAGGGTCC AGCAGAAGGA AACATGGCTG

CCAAAGTGTT TGAGTCCATT GGCAAGTTTG GCCTGGCCTT

AGCTGTTGCA GGAGGCGTGG TGAACTCTGC CTTATATAAT

GTGGATGCTG GGCACAGAGC TGTCATCTTT GACCGATTCC

GTGGAGTGCA GGACATTGTG GTAGGGGAAG GGACTCATTT

TCTCATCCCG TGGGTACAGA AACCAATTAT CTTTGACTGC

CGTTCTCGAC CACGTAATGT GCCAGTCATC ACTGGTAGCA

AAGATTTACA GAATGTCAAC ATCACACTGC GCATCCTCTT

CCGGCCTGTC GCCAGCCAGC TTCCTCGCAT CTTCACCAGC

ATCGGAGAGG ACTATGATGA GCGTGTGCTG CCGTCCATCA

CAACTGAGAT CCTCAAGTCA GTGGTGGCTC GCTTTGATGC

TGGAGAACTA ATCACCCAGA GAGAGCTGGT CTCCAGGCAG

GTGAGCGACG ACCTTACAGA GCGAGCCGCC ACCTTTGGGC

TCATCCTGGA TGACGTGTCC TTGACACATC TGACCTTCGG

GAAGGAGTTC ACAGAAGCGG TGGAAGCCAA ACAGGTGGCT

CAGCAGGAAG CAGAGAGGGC CAGATTTGTG GTGGAAAAGG

CTGAGCAACA GAAAAAGGCG GCCATCATCT CTGCTGAGGG

CGACTCCAAG GCAGCTGAGC TGATTGCCAA CTCACTGGCC

ACTGCAGGGG ATGGCCTGAT CGAGCTGCGC AAGCTGGAAG

CTGCAGAGGA CATCGCGTAC CAGCTCTCAC GCTCTCGGAA

CATCACCTAC CTGCCAGCGG GGCAGTCCGT GCTCCTCCAG

CTGCCCCAGT GAGGGCCCAC CCTGCCTGCA CCTCCGCGGG

CTGACTGGGC CACAGCCCCG ATGATTCTTA ACACAGCCTT

CCTTCTGCTC CCACCCCAGA AATCACTGTG AA          992
```

It is of note that this promoter was selected because it has been used before to develop WAT specific animal models.

The inventors have shown that prohibitin has an important role in adipogenesis/overexpression of prohibitin in 3T3-L1 cell culture system increases adipogenesis. Furthermore, mitochondrial biogenesis is involved in adipogenesis and prohibitin is known to have a role in mitochondrial biogenesis. Thus, the inventors' hypothesis was that overexpression of prohibitin in WAT will upregulate mitochondrial biogenesis and will leads to obesity development.

Generation of Mito-Ob Transgenic Mice

The aP2 promoter containing PHB clone was digested with Sac1 and Kpn1 to release the fragment containing aP2 promoter with full length PHB. The aP2-PHB DNA was purified and used to generate Mito-Ob mice by pro-nuclear injection of aP2-PHB DNA in CD1 zygotes. This procedure was carried out at the transgenic and knockout mice facility at University of Manitoba, Winnipeg, Canada. Founder animals were identified by PCR amplification of tail genomic DNA using the following primers. Forward Primer: 5' GCAGCCCGGGGGATCCACTA 3' (SEQ ID NO:3) and Reverse Primer: 5' GCACACGCTCATCAAAGTCCTCTC-CGATGCTG 3' (SEQ ID NO:4).

Founder male mice were mated with CD1 female mice to obtain the Mito-Ob transgenic progeny as per standard protocol. The Mito-Ob transgenic mice were identified by genotyping the tail DNA by PCR using above-mentioned primers. All the procedures involving Mice were done according to the animal use protocol of the University of Manitoba, Winnipeg, Canada.

Figure 4:
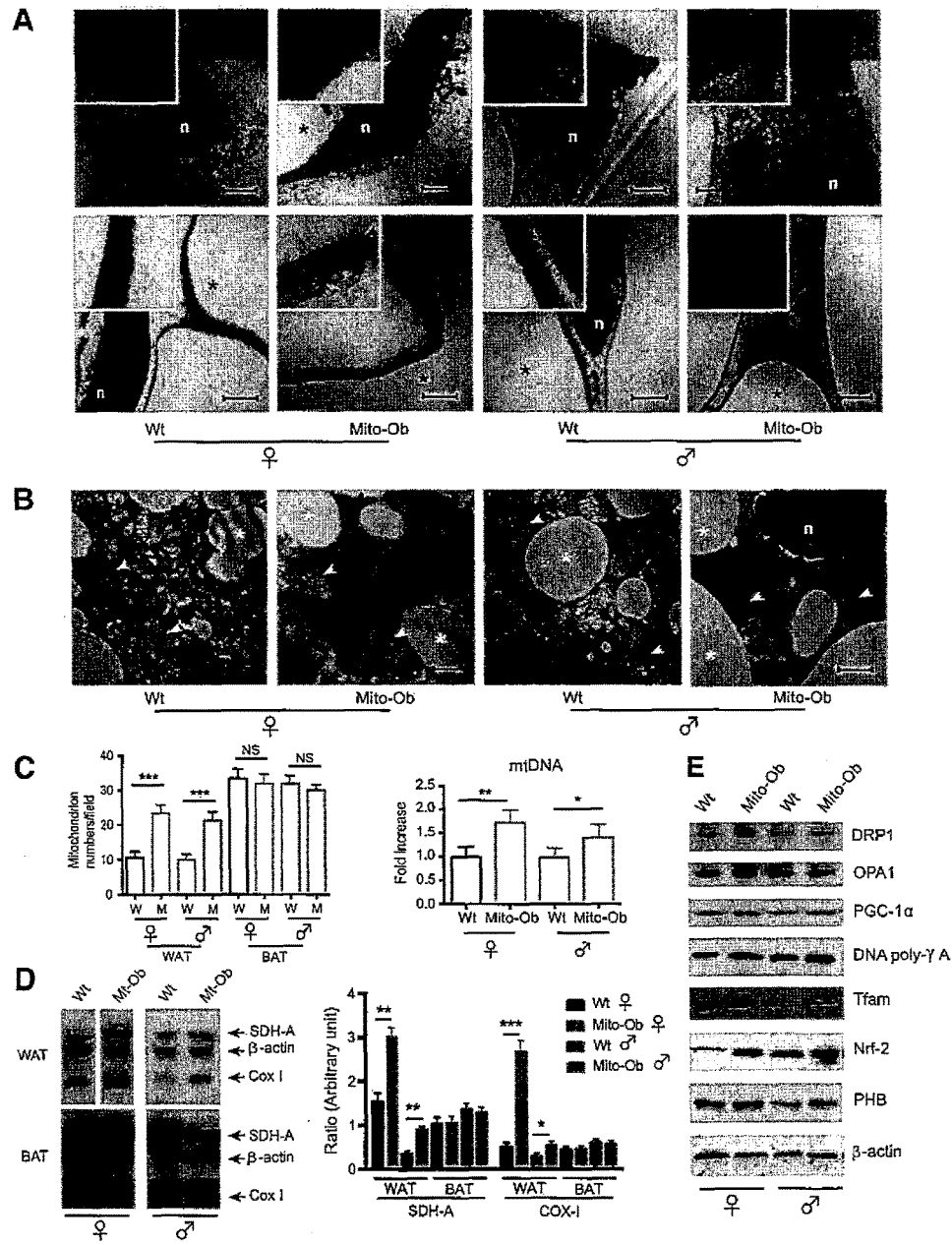
FIG. 4. Ultrastructural analysis of adipose tissue from the Mito-Ob mice. (A) Representative transmission electron micrographs (magnification 13,500×) of WAT showing relative distribution of mitochondria (shown with ➤) in adipocytes from Mito-Ob and Wt mice (n=5 mice in each group). * Indicates unilocular lipid droplets, n indicates nucleus. Further magnified view is shown in the inset in each case. Scale bars, 1 µm. (B) Representative transmission electron micrographs (magnifications 19,000×) of BAT showing changes in mitochondrial cristae structure (white arrowhead) and larger fat droplet size (white asterisk) in Mito-Ob mice in comparison with Wt mice (n=5 mice in each group). Scale bars 500 nm. (C) Histograms showing mitochondrial numbers, and mtDNA copy numbers in the WAT of Mito-Ob and Wt mice as determined by real-time PCR (n=5). (D) Representative immunoblots and histograms showing the expression levels of SDH-A and COX-I in the adipose tissue of Mito-Ob mice (the ratio of SDH-A or COX-I in relation to beta-actin; n=4 in each group). (E) Representative immunoblots showing expression level of marker proteins of mitochondrial biogenesis, fission and fusion (n=4). * P<0.05,  P<0.01, * P<0.001 by Student's t test. Data are presented as mean±SEM.

As discussed above, FIG. 4 demonstrates that overexpression of PHB in WAT upregulates mitochondrial biogenesis. Specifically, panels A-C are representative transmission electron micrographs (TEM) of adipocytes from Mito-Ob mouse showing an abundance of mitochondria in the different areas of adipocyte. This can be contrasted with panel D, a TEM of adipocyte from wild-type (Wt) mouse which is shown as a control.

FIG. 3C demonstrates the increased adipose depot weight in Mito-Ob mice. Histograms showing brown fat (BF), sub-cutaneous fat (SCF) and visceral fat (VF) weight from Mito-Ob mice in comparison to their wild-type littermates. As can be seen, all types of fat are increased significantly.

Figure 2:
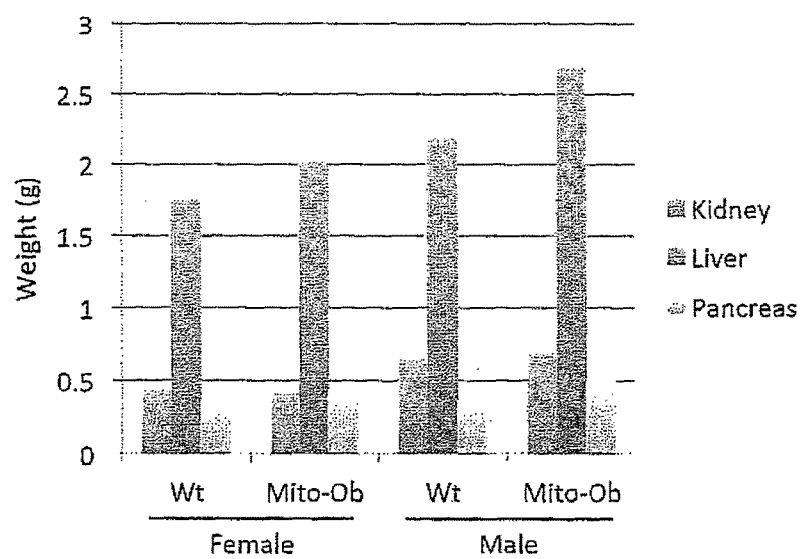
FIG. 2. Histograms showing kidney, liver and pancreas weight from Mito-Ob mice in comparison to their wild-type littermates. Average values of five animals in each group are shown.

FIG. 2 provides histograms showing kidney, liver and pancreas weight from Mito-Ob mice in comparison to their wild-type littermates. Average values of five animals in each group are shown. As can be seen, there is a noticeable increase in the weight of the liver.

Figure 5:
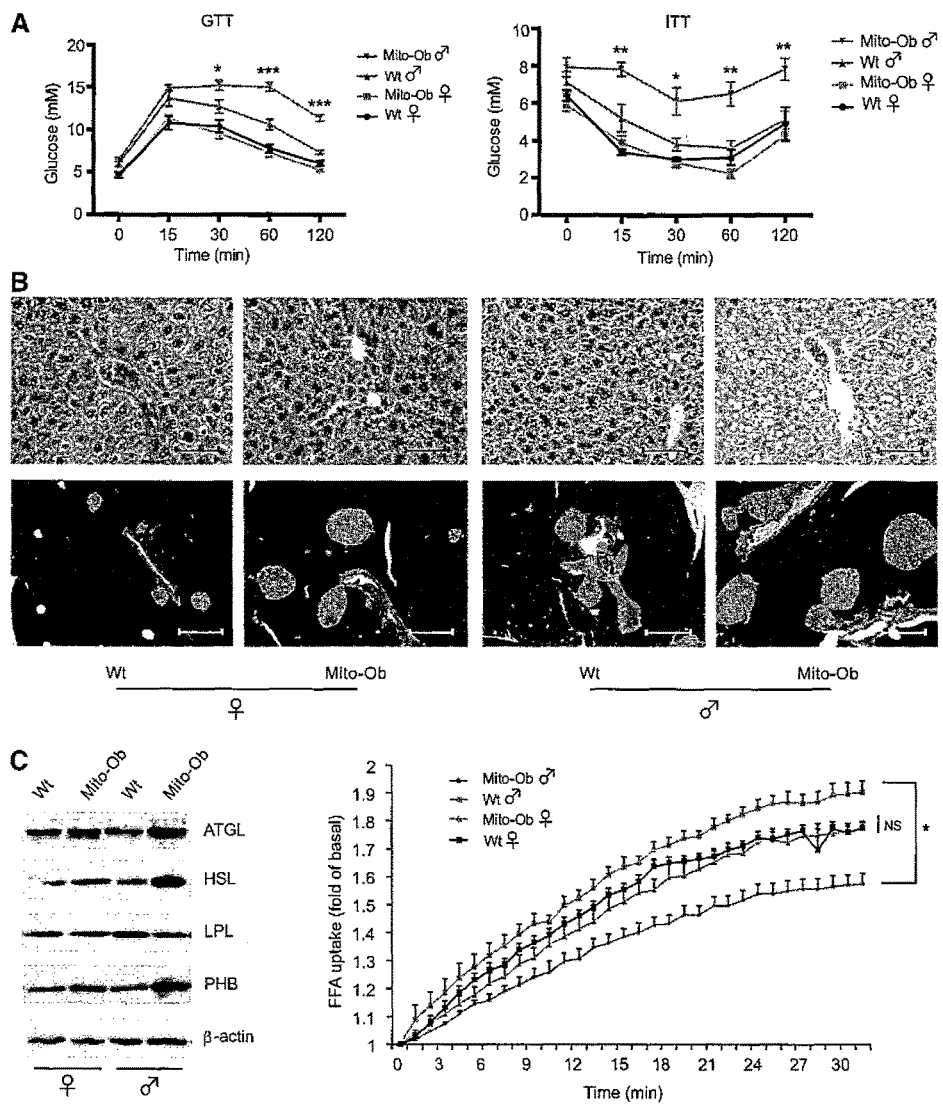
FIG. 5. The metabolic phenotype of the Mito-Ob mice at six months of age. (A) Line graphs showing glucose tolerance test (GTT, n=9 to 12 mice in each group) and insulin tolerance test (ITT, n=7 to 9 mice in each group) in Mito-Ob mice in comparison with Wt mice. Asterisks indicate comparison between Mito-Ob vs Wt male mice. * P<0.05,  P<0.01, * P<0.001 by Student's t test. Data are presented as mean±SEM. (B) Representative photomicrographs showing hematoxylin-eosin stained histological sections of liver (upper panel, scale bars, 20 µm) and pancreas (lower panel, scale bars, 50 µm) from Mito-Ob and Wt mice. (n=6 mice per group). (C) Representative immunoblots showing expression levels of different lipases in the WAT from Mito-Ob and Wt mice (n=4). Beta-actin blot is included as loading control. Line graphs insulin-induced free fatty acid uptake by WAT from Mito-Ob and Wt mice. Data are presented as mean±SEM (n=4). NS—Not significant. *Significantly different during entire time course (P<0.05-0.001).

As can be seen in FIG. 5A, Mito-Ob mice have impaired glucose metabolism. Line graphs showing glucose tolerance test (GTT) in Mito-Ob males and females in comparison to their wild-type littermates. Average values of five animals in each group are shown. Specifically, Mito-Ob mice are slower to clear glucose from their blood.

As can be seen in FIG. 5A, Mito-Ob male mice develop insulin resistance. Line graphs showing insulin tolerance test (ITT) in Mito-Ob males and females in comparison to their wild-type littermates. Average values of five animals in each group are shown. Specifically, the Mito-Ob mice are slower to clear glucose from their blood in response to insulin injection.

Growth Curve and Adipose Tissue Weight

Both male and female Mito-Ob mice initially weighed similar to their wild-type littermates; however, they started to gain weight around one month onwards and became significantly obese (P<0.001) by 2-3 months of age (FIG. 3A, FIG. 3B), without any founder effect (FIG. 3A). No difference in food intake was found between Mito-Ob and wild-type mice (FIG. 3B); however, a reduction in horizontal activity levels was observed in Mito-Ob mice (FIG. 3B). These results suggest that PHB overexpression in mice adipocytes leads to obesity development independent of food intake.

Female Mito-Ob mice accumulated more visceral fat, but less BAT, than male Mito-Ob mice (FIG. 3C), whereas subcutaneous fat mass increased similarly in Mito-Ob female and male mice (FIG. 3C). Collectively, these data indicate that PHB overexpression in mice adipocytes leads to increased adipose tissue mass, with sex related differential effects on brown and visceral fat depots.

Histology of Adipose Tissue

Consistent with an increase in the adipose tissue mass in Mito-Ob mice, adipocyte hypertrophy was apparent in the WAT from Mito-Ob mice (FIG. 3D). In addition, WAT from male Mito-Ob mice showed increased distribution of crown like structures, a sign of macrophage infiltration (FIG. 3D). Male Mito-Ob mice also had increased fat accumulation in BAT (FIG. 3D). These data indicate that PHB overexpression in adipocytes leads to adipocyte hypertrophy, implying increased triglycerides synthesis and/or storage in WAT of Mito-Ob mice.

Ultrastructural Analysis of Adipose Tissue

TEM showed an increase in mitochondrial number and their distribution throughout the cytoplasmic rim of white adipocytes in Mito-Ob mice vs. wild-type controls (FIG. 4A). The mitochondria in these adipocytes were predominantly elongated in Mito-Ob, but round in wild-type mice (FIG. 4A). In contrast, BAT had similar mitochondrial content in Mito-Ob and wild-type mice (FIG. 4B). However, a reduction in mitochondrial size was observed in BAT from Mito-Ob male mice (FIG. 4B).

To confirm mitochondrial biogenesis in the WAT of Mito-Ob mice, mitochondrial DNA copy numbers and mitochondrial protein (SDH-A, Cox-I, (PGC-1α, DNA poly-γ A, Tfam etc.) levels were determined. Both were significantly upregulated (P<0.05-0.001) in Mito-Ob mice (FIG. 4C-E). Collectively, these results indicate that PHB overexpression in adipocytes induces mitochondrial biogenesis.

Systemic Metabolism in Mito-Ob Mice

Only Mito-Ob males were found to have significantly impaired glucose (P<0.05-0.001) and insulin (P<0.05-0.01) tolerance (FIG. 5A). Mito-Ob female mice had insulin sensitivity similar to wild-type animals (FIG. 5A). A sign of hepatic steatosis was also found in the liver of Mito-Ob mice (FIG. 5B). The data indicates that obesity in Mito-Ob mice have sex specific metabolic impairment. Among lipid parameters, serum triglycerides, glycerol and cholesterol levels were significantly decreased (P<0.001) in Mito-Ob female mice, whereas free fatty acid levels were significantly increased (P<0.01) in Mito-Ob male mice (Table 1).

Serum insulin levels were significantly higher (P<0.01) in Mito-Ob male mice vs. wild-type littermates (Table 1). However, Mito-Ob female mice had insulin levels as wild-type littermates (Table 1). Among adipokines, adiponectin levels were increased (P<0.05) only in Mito-Ob female mice (Table 1), whereas leptin levels were higher in Mito-Ob male mice than in females (Table 1). Resistin levels were unchanged in the Mio-Ob male mice (Table 1).

WAT Lipase Levels in the Mito-Ob Mice

Next, the expression levels of adipose triglyceride lipase (ATGL), hormone sensitive lipase (HSL) and lipoprotein lipase (LPL) in WAT were analyzed. ATGL and HSL were upregulated in both male and female Mito-Ob mice vs. wild-type mice; however, their levels were higher in Mito- Ob male mice than Mio-Ob female mice (FIG. 5C). LPL protein levels were decreased in Mito-Ob male mice, whereas LPL levels remain unchanged in Mito-Ob female mice (FIG. 5C). FFA uptake was significantly decreased in Mito-Ob male (FIG. 5C) without any significant change in fatty acid oxidation.

Materials and Methods

Body Weight and Food Intake.

The animals were given normal chow (LabDiet, St. Louis, Mo.). Body weight of Mito-Ob and wild-type mice was recorded on a weekly basis after weaning and food intake during 3 to 6 months of age was determined (Chen and Nyomba, 2003).

Physical Activity.

Horizontal activity levels were measured using a metabolic cage system (AccuScan, Columbus, Ohio), and data were collected for every 5 minutes for 24 hours (Kim et al., 2008).

Histology.

Adipose tissues from six months old Mito-Ob and Wt littermates were fixed in buffered formaldehyde and subsequently dehydrated, embedded in paraffin, and 5 µm sections were stained with hematoxylin-eosin (Nguyen at al., 2011).

Western Immunoblotting.

Adipose tissue lysates from Mito-Ob and wild-type mice containing equal amount of proteins (~15 µg/lane) were separated by SDS-PAGE and subsequently analyzed by immunoblotting (Ande et al., 2012; Nguyen et al., 2011). MitoBiogenesis™ Western blot cocktail (Abcam Inc.) was used to determine succinate dehydrogenase-A (SDH-A) and cytochrome c oxidase-I (COX-I) protein levels in adipose tissue.

Transmission Electron Microscopy (TEM).

Adipose tissues were excised into small pieces (<1 mm$^3$) and fixed with 2.5% glutaraldehyde in 0.1 M PBS buffer (pH 7.4) for 3 hours. Each specimen was post-fixed in 1% osmium tetroxide for 1 hour before embedding in Epon resin. TEM was performed with a Philips CM10, at 80 kV, on ultra-thin sections (100 nm) and stained with uranyl acetate and counterstained with lead citrate.

Mitochondrial DNA (mtDNA).

mtDNA copy number in adipose tissue was determined by real-time PCR (Kelly et al., 2012).

Measurement of Adipokines and Hormones.

Serum adipokines and hormones were measured using mouse Bio-Plex Pro™ Assays Diabetes panel and Bio-Plex 200™ multiplex suspension array systems (Bio-Rad, Hercules, Calif.) as per manufacturer's protocols.

Glucose and Insulin Tolerance Tests (GTT and ITT).

GTT and ITT in 6 months old mice were performed as s described (Nguyen et al., 2011).

Measurement of Cholesterol, Triglycerides and Free Fatty Acids (FFA).

Serum cholesterol (Molecular Probes, Eugene, Oreg.), triglycerides and free fatty acid levels were measured using kits from BioAssay Systems (Hayward, Calif.). FFA uptake and oxidation were measured using kits from (Abcam Inc.).

Statistical Analysis.

All statistical analyses were performed using GraphPad Prism 6. Experimental results are shown as mean±SEM. Two-tailed Student's unpaired t-tests were performed to compare sex-matched Mito-Ob and wild-type littermates, unless indicated otherwise. P<0.05 was considered significant.

The scope of the claims should not be limited by the preferred embodiments set forth in the examples, but should be given the broadest interpretation consistent with the description as a whole.

TABLE 1

Serum hormones, adipokines and lipid profile in Mito-Ob and Wt mice at 6 months of age. Data are presented as mean ± SEM (n = 5 to 9 in each group).

| | Female | | | | Male | | | |
|---|---|---|---|---|---|---|---|---|
| | Wt | | Mito-Ob | | Wt | | Mito-Ob | |
| | Fasting | Fed | Fasting | Fed | Fasting | Fed | Fasting | Fed |
| Insulin (ng/ml) | 1.1 ± 0.1 | 3.1 ± 0.7 | 1.3 ± 0.2 | 3.8 ± 0.9 | 1.6 ± 0.3 | 7.5 ± 0.9 | 6.58 ± 0.9** | 14.3 ± 1.5** |
| Glucagon (ng/ml) | 0.7 ± 0.1 | 0.6 ± 0.1 | 0.5 ± 0.04 | 0.6 ± 0.1 | 0.3 ± 0.04 | 0.4 ± 0.03 | 0.4 ± 0.03 | 0.3 ± 0.03 |
| Ghrelin (ng/ml) | 5.3 ± 0.5 | 2.6 ± 0.5* | 11.6 ± 1.6* | 2.8 ± 0.8 | 4.8 ± 0.4 | 2.3 ± 0.3 | 2.7 ± 0.3*** | 0.7 ± 0.1*** |
| GIP (ng/ml) | 0.4 ± 0.08 | 0.3 ± 0.04 | 0.3 ± 0.03 | 0.3 ± 0.06 | 0.4 ± 0.09 | 0.3 ± 0.03 | 0.3 ± 0.04 | 0.6 ± 0.08* |
| GLP-1 (ng/ml) | 0.3 ± 0.05 | 0.2 ± 0.02 | 0.2 ± 0.02 | 0.2 ± 0.05 | 0.1 ± 0.01 | 0.2 ± 0.02 | 0.2 ± 0.03 | 0.2 ± 0.03 |
| Adiponectin (µg/ml) | 12.3 ± 0.5 | 6.0 ± 0.6 | 14.3 ± 1.9 | 8.3 ± 0.6* | 6.3 ± 0.2 | 4.8 ± 0.2 | 7.2 ± 0.4 | 5.6 ± 0.6 |
| Leptin (ng/ml) | 7.5 ± 1.5 | 4.9 ± 1.0 | 6.1 ± 1.7 | 8.6 ± 1.3 | 8.6 ± 2.1 | 11.0 ± 2.8 | 14.4 ± 1.0* | 14.2 ± 1.6 |
| Resistin (ng/ml) | 2.4 ± 0.3 | 1.1 ± 0.1 | 1.8 ± 0.2 | 1.9 ± 0.1 | 1.1 ± 0.1 | 1.2 ± 0.1 | 0.8 ± 0.1 | 1.1 ± 0.1 |
| Cholesterol (µg/ml) | 648 ± 19.0 | 716 ± 18.8 | 558 ± 69.1 | 594 ± 35.3* | 508 ± 59.4 | 748 ± 58.8 | 600 ± 59.2 | 643 ± 20.6 |
| Free fatty acids (mM) | 0.8 ± 0.1 | 0.7 ± 0.1 | 0.9 ± 0.2 | 0.4 ± 0.1 | 0.9 ± 0.2 | 0.9 ± 0.1 | 0.8 ± 0.1 | 1.6 ± 0.1** |
| Glycerol (mM) | 1.4 ± 0.08 | 1.1 ± 0.12 | 0.6 ± 0.04*** | 0.5 ± 0.04*** | 0.6 ± 0.14 | 1.0 ± 0.04 | 0.8 ± 0.02 | 0.7 ± 0.09 |

TABLE 1-continued

Serum hormones, adipokines and lipid profile in Mito-Ob and Wt mice at 6 months of age. Data are presented as mean ± SEM (n = 5 to 9 in each group).

| | Female | | | | Male | | | |
| --- | --- | --- | --- | --- | --- | --- | --- | --- |
| | Wt | | Mito-Ob | | Wt | | Mito-Ob | |
| | Fasting | Fed | Fasting | Fed | Fasting | Fed | Fasting | Fed |
| Triglycerides (mM) | 1.4 ± 0.23 | 1.4 ± 0.23 | 0.4 ± 0.04*** | 0.3 ± 0.05*** | 1.1 ± 0.14 | 1.5 ± 0.15 | 1.5 ± 0.08 | 1.0 ± 0.16 |

Asterisk signs applicable to both sexes (Mito-Ob) in comparison with respective wild-type mice. Comparison shown are sex matched fasting vs. fasting or fed vs fed between Wt and Mito-Ob.
*$P < 0.05$,
**$P < 0.01$,
***$P < 0.001$ by Student's t test.

REFERENCES

Ande S R, Xu Z, Gu Y, Mishra S. Prohibitin has an important role in adipocyte differentiation. International Journal of Obesity (2012) 36: 123-1244.

Artal-Sanz M, Tavernarakis N. Prohibitin couples diapause signalling to mitochondrial metabolism during ageing in C. elegans. Nature 2009; 461: 793-797.

Athale J, Ulrich A, Chou Macgarvey N, Bartz R R, Welty-Wolf K E, Suliman H B, Piantadosi C A (2012) Nrf2 promotes alveolar mitochondrial biogenesis and resolution of lung injury in Staphylococcus aureus pneumonia in mice. Free Radic Biol Med 53: 1584-1594.

Bjorntorp, P. (1996). The regulation of adipose tissue distribution in humans. Int. J Obes Relat Metab Disord 20: 291-302.

Boerschmann H, Pfluger M, Henneberger L, Ziegler A G, Hummel S: Prevalence and predictors of overweight and insulin resistance in offspring of mothers with gestational diabetes mellitus. Diabetes Care 2010, 33:1845-1849.

Brown W V, Fujioka K, Wilson P W, and Woodworth K A, "Obesity: why be concerned?" The American Journal of Medicine, vol. 122, no. 4, pp. S4-S11, 2009.

Chen J Q, Cammarata P R, Baines C P, Yager J D (2009) Regulation of mitochondrial respiratory chain biogenesis by estrogens/estrogen receptors and physiological, pathological and pharmacological implications. Biochim Biophys Acta 1793: 1540-1570.

Chen L, Nyomba B L (2003) Effects of prenatal alcohol exposure on glucose tolerance in the rat offspring. Metabolism 52: 454-62.

Chua S, Herberg L, Leiter E H. Obesity/diabetes in mice with mutations in leptin or leptin receptor genes. In Shafrir E (ed). Animal models of Diabetes Frontiers in Research. London: Boca Raton, Fla. CRC; 2007. p 61-102.

De Pauw, A. et al. (2009) Mitochondrial (dys)function in adipocyte (de)differentiation and systemic metabolic alterations. Am. J. Pathol. 175, 927-939.

Dong P, Jiang L, Liu J, Wu Z, Guo S, Zhang Z, Zhou F, Liu Z. Induction of Paclitaxel Resistance by ERα Mediated Prohibitin Mitochondrial-Nuclear Shuttling. PLoS One. 2013 Dec. 23; 8(12):e83519.

Fu Y, Luo L, Luo N, Garvey W T. Lipid metabolism mediated by adipocyte lipid binding protein (ALBP/aP2) gene expression in human THP-1 macrophages. Atherosclerosis. 2006 September; 188(1):102-11.

Fu Y, Luo N, Klein R L, Garvey W T (2005) Adiponectin promotes adipocyte differentiation, insulin sensitivity, and lipid accumulation. J Lipid Res 46: 1369-1379.

Guh D P, Zhang W, Bansback N, Amarsi Z, Birmingham C L, and Anis A H, "The incidence of co-morbidities related to obesity and overweight: a systematic review and meta-analysis," BMC Public Health, vol. 9, article 88, 2009.

Guilherme A, Virbasius J V, Puri V, Czech M R Adipocyte dysfunctions linking obesity to insulin resistance and type 2 diabetes. Nat Rev Mol Cell Biol 2008; 9:367-377.

Hummel K P, Dickie M M, Coleman D L. Diabetes, a new mutation in the mouse. Science 1966; 153: 1127-8.

Jitrapakdee S, Vidal-Puig A, Wallace J C. Anaplerotic roles of pyruvate carboxylase in mammalian tissues. Cell Mol Life Sci 2006; 63: 843-854.

Kanasaki K, Koya D. Biology of obesity: lessons from animal models of obesity. J Biomed Biotechnol. 2011; 2011:197636.

Kanavos P, van den Aardweg S, Schurer W (2012) Diabetes expenditure, burden of disease and management in 5 EU countries. LSE Health, London School of Economics.

Kang T, Lu W, Xu W, Anderson L, Bacanamwo M, Thompson W, Chen Y E, Liu D. MicroRNA-27 (miR-27) targets prohibitin and impairs adipocyte differentiation and mitochondrial function in human adipose-derived stem cells. J Biol Chem. 2013 Nov. 29; 288(48):34394-402.

Kasashima K, Sumitani M, Satoh M, Endo H (2008) Human prohibitin 1 maintains the organization and stability of the mitochondrial nucleoids. Exptl Cell Res 314: 988-996.

Kelly R D W, Mahmud A, McKenzie M, Trouche I A, St John J C (2012) Mitochondrial DNA copy number is regulated in a tissue specific manner by DNA methylation of the nuclear-encoded DNA polymerase gamma A. Nucleic Acid Research 40:10124-10138.

Kim E R, Leckstrom A, Mizuno T M. Impaired anorectic effect of leptin in neurotensin receptor 1-deficient mice. Behav Brain Res. 2008 Dec. 1; 194(1):66-71.

Kopelman P, "Health risks associated with overweight and obesity," Obesity Reviews, vol. 8, no. 1, pp. 13-17, 2007.

Kusminski et al. MitoNEET-driven alterations in adipocyte mitochondrial activity reveal a crucial adaptive process that preserves insulin sensitivity in obesity. Nat Med. 2012 October; 18(10):1539-49.

Kusminski C M, Scherer P E. Mitochondrial dysfunction in white adipose tissue. Trends in Endocrinology and Metabolism 23 (2012) 435-43.

Levin B E: Metabolic imprinting: critical impact of the perinatal environment on the regulation of energy homeostasis. Philos Trans R Soc Lond B Biol Sci 2006, 361:1107-1121.

Liu D, Lin Y, Kang T, Huang B, Xu W, Garcia-Barrio M, Olatinwo M, Matthews R, Chen Y E, Thompson W E. Mitochondrial dysfunction and adipogenic reduction by prohibitin silencing in 3T3-L1 cells. PLoS One. 2012; 7(3):e34315.

Lu, R. H. et al. (2010) Mitochondrial development and the influence of its dysfunction during rat adipocyte differentiation. Mol. Biol. Rep. 37, 2173-2182.

Merkwirth C, Langer T. Prohibitin function within mitochondria: essential roles for cell proliferation and cristae morphogenesis. Biochim Biophys Acta 2009; 1793:27-32.

Nguyen K H, Yao X H, Moulik S, Mishra S, Nyomba B L (2011) Human IGF binding protein-3 overexpression impairs glucose regulation in mice via an inhibition of insulin secretion. Endocrinology 152: 2184-2196.

Nilsson C et al. Laboratory animals as surrogate models of human obesity. Acta Pharmacologica Sinica (2012) 33: 173-181.

Perusse L, Rice T, Chagnon Y C, Despres J P, Lemieux S, Roy S et al. A genome-wide scan for abdominal fat assessed by computed tomography in the que'bec family study. Diabetes 2001; 50: 614-21.

Pulgarón E R. Childhood obesity: a review of increased risk for physical and psychological comorbidities. Clin Ther. 2013 January; 35(1):A18-32.

Rong J X, Qiu Y, Hansen M K, Zhu L, Zhang V, Xie M et al. Adipose mitochondrial biogenesis is suppressed in db/db and high-fat diet-fed mice and improved by rosiglitazone. Diabetes 2007; 56: 1751-60.

Sato T, Saito H, Swensen J, Olifant A, Wood C, Danner D et al. The human prohibitin gene located on chromosome 17q21 is mutated in sporadic breast cancer. Cancer Res 1992; 52: 1643-1646.

Shafrir E, Ziv E. A useful list of spontaneously arising animal models of obesity and diabetes. Am J Physiol Endocrinol Metab. 2009 June; 296(6):E1450-2.

Soubry A et al. Paternal obesity is associated with IGF2 hypomethylation in newborns: results from a Newborn Epigenetics Study (NEST) cohort BMC Medicine 2013, 11:29 doi:10.1186/1741-7015-11-29

Sun, K. et al. (2011) Adipose tissue remodeling and obesity. J. Clin. Invest. 121, 2094-2101.

Tanumihardjo S A, Anderson C, Kaufer-Horwitz M, Bode L, Emenaker N J, Haqq A M, Satia J A, Silver H J, Stadler D D: Poverty, obesity, and malnutrition: an international perspective recognizing the paradox. J Am Diet Assoc 2007, 107:1966-1972.

Theiss A L, Vijay-Kumar M, Obertone T S, Jones D P, Hansen J M, Gewirtz A T, Merlin D, Sitaraman S V (2009) Prohibitin is a novel regulator of antioxidant response that attenuates colonic inflammation in mice. Gastroenterology 137: 199-208.

Trayhurn P, Jones P M, McGuckin M M, Goodbody A E. Effects of overfeeding on energy balance and brown fat thermogenesis in obese (ob/ob) mice. Nature 1982; 295: 323-5.

Vessal M, Mishra S, Moulik S, Murphy L W Prohibitin attenuates insulin-stimulated glucose and fatty acid oxidation in adipose tissue by inhibition of pyruvate decarboxylase. FEBS J 2006; 273: 568-576.

Wang C H, Wang C C, Huang H C, Wei Y H (2013) Mitochondrial dysfunction leads to impairment of insulin sensitivity and adiponectin secretion in adipocytes. FEBS J 280: 1039-1050.

Wilson-Fritch L et al. Mitochondrial remodeling in adipose tissue associated with obesity and treatment with rosiglitazone. J. Clin. Invest. 114:1281-1289 (2004).

Yao J, Zhao L, Mao Z, Chen S, Wong K C, To J, Brinton R D (2013) Potentiation of brain mitochondrial function by S-equol and R/S-equol estrogen receptor β-selective phytoSERM treatments. Brain Res 1514: 128-141.

---

The invention claimed is:

1. A transgenic mouse whose genome comprises a nucleic acid sequence encoding prohibitin operably linked to an adipocyte protein 2 (aP2) promoter, wherein the mouse has increased adipose tissue mass as compared to a wild type mouse.

2. The transgenic mouse according to claim 1 wherein the prohibitin gene comprises the nucleotide sequence as set forth in SEQ ID No:2.

3. The transgenic mouse according to claim 1 wherein the aP2 promoter comprises the nucleotide sequence as set forth in SEQ ID No:1.

4. The transgenic mouse according to claim 1 wherein the exogenous nucleic acid construct is integrated into the mouse genome.

5. A transgenic mouse, comprising a transgene, said transgene comprising a polynucleotide encoding a mouse prohibitin protein operably linked to a mouse adipocyte protein 2 (aP2) promoter, wherein said transgenic mouse develops increased adipose tissue mass and obesity compared to a wild type mouse of the same strain.

6. The transgenic mouse according to claim 5 wherein the prohibitin protein comprises an amino acid sequence deduced from the nucleotide sequence as set forth in SEQ ID No:2.

7. The transgenic mouse according to claim 5 wherein the aP2 promoter comprises the nucleotide sequence as set forth in SEQ ID No:1.

8. The transgenic mouse according to claim 5 wherein the transgene is integrated into the mouse genome.

9. A mouse transgenic fertilized egg comprising an expression construct comprising (a) a nucleotide sequence encoding prohibitin and (b) a mouse adipocyte protein 2 (aP2) promoter said mouse transgenic fertilized egg capable of becoming a transgenic mouse developing increased adipose tissue mass and obesity as compared to a wild type mouse of the same strain.

10. The mouse transgenic fertilized egg according to claim 9 wherein the nucleotide sequence encoding prohibitin comprises the nucleotide sequence as set forth in SEQ ID No:2.

11. The mouse transgenic fertilized egg according to claim 10 wherein the aP2 promoter comprises the nucleotide sequence as set forth in SEQ ID No:1.

12. The mouse transgenic fertilized egg according to claim 9 wherein the expression construct is integrated into the genome of the mouse transgenic fertilized egg.

* * * * *